United States Patent [19]

Lindberg et al.

[11] 4,060,082
[45] Nov. 29, 1977

[54] DUAL-INGREDIENT MEDICATION DISPENSER

[75] Inventors: Richard M. Lindberg, Des Plaines; Srinivas T. Raghavachari, Chicago, both of Ill.

[73] Assignee: MPL, Inc., Chicago, Ill.

[21] Appl. No.: 714,661

[22] Filed: Aug. 16, 1976

[51] Int. Cl.² .............................................. A61M 5/00
[52] U.S. Cl. .............................. 128/218 M; 128/272.1; 141/388
[58] Field of Search ....... 128/218 R, 218 M, 218 DA, 128/218 D, 215, 216, 224, 236, 247, 272.1, 272.3; 141/2, 27, 311 R, 312, 388

[56] References Cited

U.S. PATENT DOCUMENTS

| | | | |
|---|---|---|---|
| 1,718,593 | 6/1929 | Smith | 128/272.1 |
| 2,724,383 | 11/1955 | Lockhart | 128/272.1 X |
| 3,552,387 | 1/1971 | Stevens | 128/218 M |
| 3,610,297 | 10/1971 | Raaf et al. | 141/27 |
| 3,729,031 | 4/1973 | Baldwin | 141/2 |
| 3,729,032 | 4/1973 | Tischlinger et al. | 141/2 |

Primary Examiner—John D. Yasko
Attorney, Agent, or Firm—Kinzer, Plyer, Dorn & McEachran

[57] ABSTRACT

A dual-ingredient dispenser for medication and other applications, comprising two syringes joined by a releasable connecting sleeve; one syringe, used for mixing and dispensing the medication, comprises a housing with inlet and outlet valve-seal members at its opposite ends, containing a first medication ingredient in a mixing chamber between the valve-seal members, with the inlet valve-seal member being actuatable from closed to open condition by a fill needle; the other syringe is a carrier syringe filled with a second medication ingredient and equipped with a fill needle held in alignment with the inlet valve-seal member of the first syringe.

9 Claims, 13 Drawing Figures

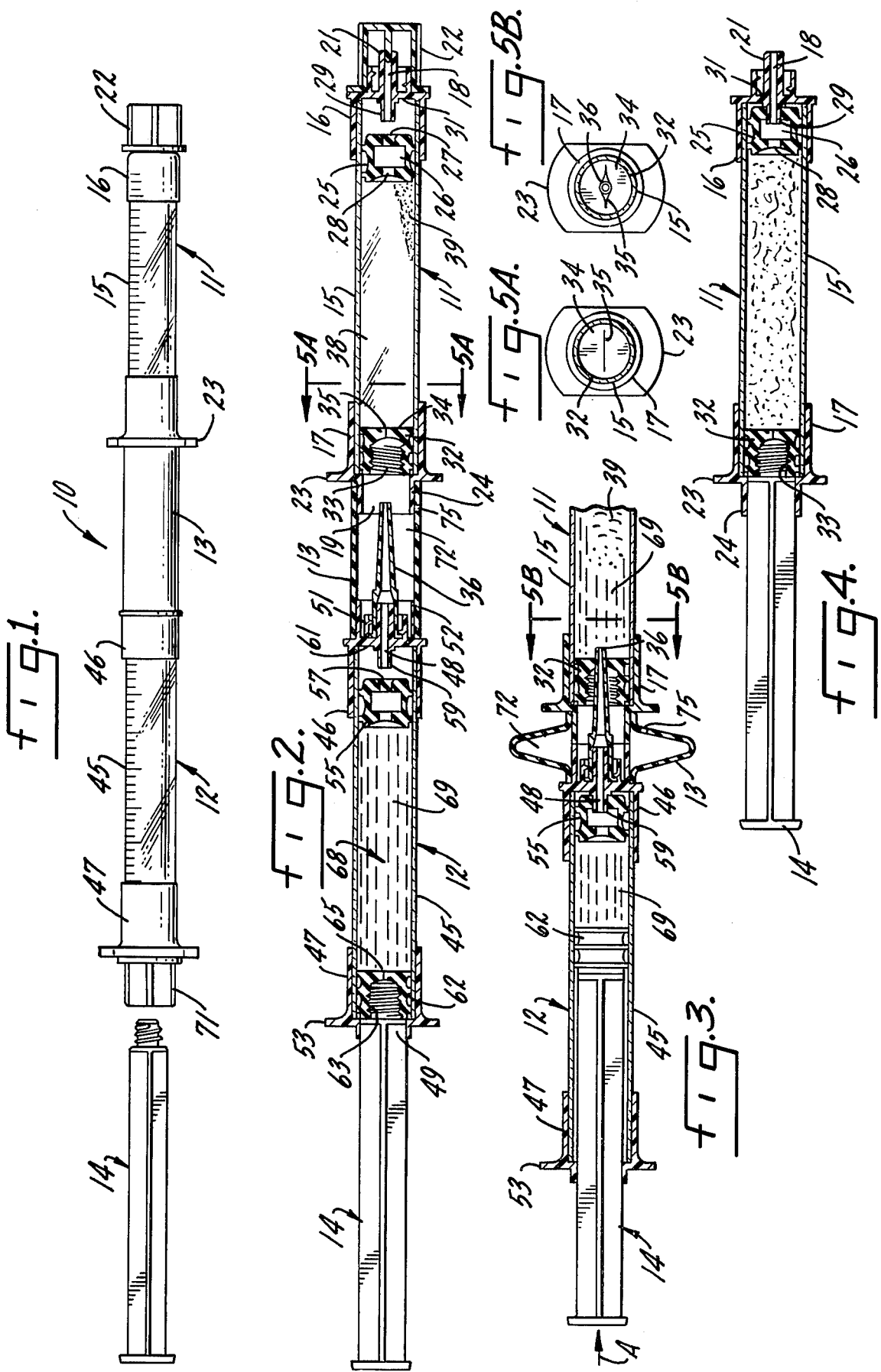

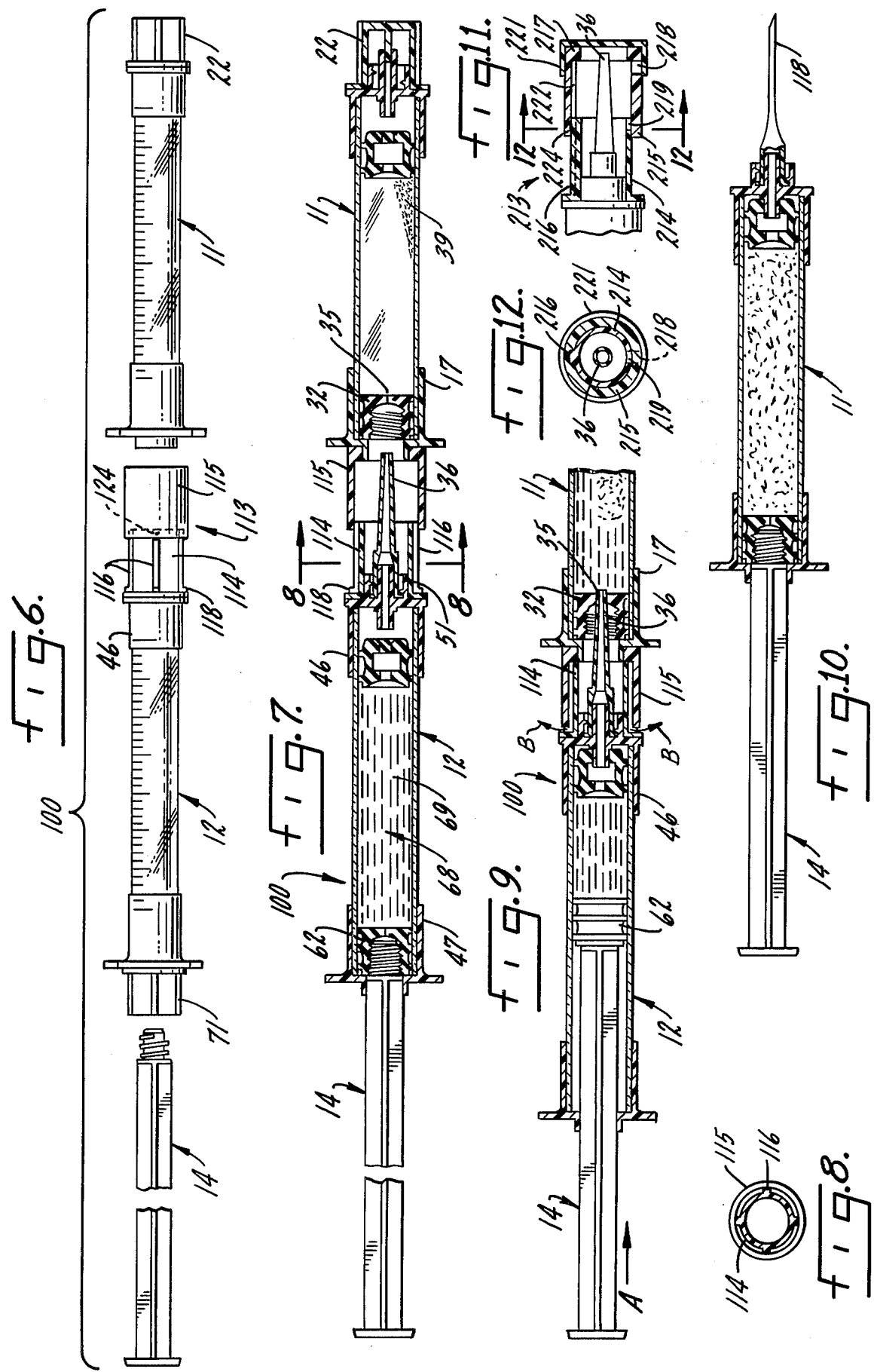

DUAL-INGREDIENT MEDICATION DISPENSER

BACKGROUND OF THE INVENTION

A number of medications comprise two ingredients which are not mixed together until shortly prior to administration. In many instances, one of the two ingredients comprises a solid, usually a powder, whereas the other ingredient constitutes a liquid in which the solid ingredient is dissolved. Less frequently, the medication may comprise two liquids to be mixed together.

Administration of a dual-ingredient medication of this kind can be accomplished with a conventional syringe by first loading one ingredient into the syringe, then adding the second ingredient, shaking the syringe or otherwise agitating the contents to achieve effective mixing, and subsequently dispensing the complete dual-ingredient medication mixture in the usual manner. This procedure, however, presents substantial difficulties, including possible contamination and loss of sterilization. For example, using a conventional syringe of the kind that is filled through a fill needle connected to the outlet orifice of the syringe, it is necessary to replace the needle after the first ingredient has been drawn into the syringe, in order to avoid possible contamination of the supply of the second ingredient. Even then it may be difficult to complete this procedure without rendering the outlet portion of the syringe non-sterile, particularly by extended contact with ambient air.

Another technique that can be employed utilizes a syringe of generally conventional construction in which one ingredient has initially been loaded into the syringe, usually followed by a complete sterilization procedure for the external portion of the syringe. Again, however, it is often rather difficult to load the syringe with the second ingredient without affecting the sterile characteristics of the syringe. Moreover, in both of these procedures the manipulative steps on the part of the pharmacist or nurse or doctor are complex enough so that some difficulty may be experienced.

Specialized dual-compartment syringes have been proposed for the administration of two-ingredient medications. For one specialized syringe of this kind, reference may be made to Sarnoff et al. U.S. Pat. No. 3,326,215. A dual compartment syringe of this kind, however, is relatively costly and complex in construction, requiring structural members of different configuration from those used in conventional syringes. Moreover, filling a special purpose syringe of this kind can be quite difficult and creates other problems with regard to avoidance of contamination and maintenance of sterility.

SUMMARY OF THE INVENTION

It is an object of the present invention, therefore, to provide a new and improved dual-ingredient syringe or like medication dispenser that is constructed almost entirely from conventional syringe components and requires virtually no specialized structural elements.

Another object of the invention is to provide a new and improved dual-ingredient medication dispenser that is simple and inexpensive in construction, yet effectively minimizes the problems and difficulties of the prior art with respect to contamination or non-sterility of the ingredients or dispenser components.

A further object of the invention is to provide a new and improved dual-ingredient medication dispenser for which the manipulative steps required for effective use are held to a minimum.

Accordingly, the invention relates to a dual ingredient medication dispenser comprising a mixer-dispenser syringe including a housing having an outlet end and an inlet end, a dispensing valve-seal member normally sealing the outlet end of the housing, an inlet valve-seal member normally sealing the inlet end of the housing, the inlet valve-seal member being actuatable from a normal closed condition to an open condition by engagement with a fill needle, with the mixer-dispenser syringe housing and its two valve-seal members defining a mixing chamber containing a first medication ingredient, usually a dry powder. The dispenser further comprises a carrier syringe including a housing having an outlet end and an inlet end, a fill needle projecting outwardly from the outlet end of the housing, a discharge valve-seal member normally sealing the outlet end of the housing, and a piston-seal member normally sealing the inlet end of the housing; the carrier syringe housing, the piston member, and the discharge valve-seal member define a storage chamber containing a second medication ingredient, usually a liquid. Connecting means, comprising a connecting sleeve, releasably connects the outlet end of the carrier syringe to the inlet end of the mixer dispenser syringe with the fill needle aligned with the inlet valve-seal member of the mixer-dispenser syringe; the connecting means permits movement of the two syringes together to engage the fill needle with the inlet valve-seal member of the mixer-dispenser syringe for discharge of the second medication ingredient into the mixing chamber without requiring removal of the sleeve. In some embodiments, a flexible, collapsible sleeve is used as the connecting sleeve; in others, two relatively rigid vented telescoping sleeves, preferably joined by a frangible connection, are employed.

BRIEF DESCRIPTION OF THE DRAWINGS

FIG. 1 is an elevation view of a dual-ingredient medication dispenser constructed in accordance with one embodiment of the present invention;

FIG. 2 is a longitudinal section view of the dual ingredient medication dispenser of FIG. 1;

FIG. 3 is a detail sectional view illustrating the center portion of the medication dispenser of FIGS. 1 and 2 during the transfer of a medication ingredient from one part of the dispenser to another;

FIG. 4 illustrates the mixing and dispensing portion of the medication dispenser of FIGS. 1-3 at the time of actual administration of the medication;

FIG. 5A is a detail view of the inlet valve-seal member of the mixer portion of the dispenser, taken approximately along line 5A—5A in FIG. 2, showing the valve closed;

FIG. 5B is a view similar to FIG. 5A, taken apporximately along line 5B—5B in FIG. 3, showing the valve open;

FIG. 6 is an elevation view of a dual-ingredient medication dispenser constructed in accordance with a preferred embodiment of the present invention;

FIG. 7 is a longitudinal section view of the dual ingredient medication dispenser of FIG. 6;

FIG. 8 is a detail sectional view taken approximately along line 8—8 in FIG. 7;

FIG. 9 is a detail sectional view illustrating the center portion of the medication dispenser of FIGS. 6 and 7 during the transfer of a medication ingredient from one part of the dispenser to another;

FIG. 10 illustrates the mixing and dispensing portion of the medication dispenser of FIGS. 6–9 at the time of actual administration of the medication;

FIG. 11 is a longitudinal section view of a modified syringe interconnection for another embodiment of the invention, otherwise similar to the embodiment of FIGS. 6–10; and FIG. 12 is a transverse section view taken approximately along line 12—12 in FIG. 11.

DESCRIPTION OF THE PREFERRED EMBODIMENT

FIGS. 1 through 5B illustrate a dual-ingredient medication dispenser 10 constructed in accordance with one embodiment of the present invention. Dispenser 10 comprises a mixer-dispenser syringe 11 releasably connected to and aligned with a carrier syringe 12 by a collapsible sleeve 13. Dispenser 10 is provided with a plunger rod 14 that is used with both mixer syringes 11 and 12; rod 14 is shown detached from the remainder of dispenser 10 in FIG. 1, as would normally be the case for shipment or storage of the dispenser.

The mixer-dispenser syringe 11 comprises a housing including a glass barrel 15, a molded resin outlet end sleeve 16, and a molded rein inlet end sleeve 17. The two sleeves 16 and 17 are expansion-fitted onto barrel 15, affording a liquid-tight and vapor-tight housing except for an outlet 18 and an inlet 19. In the illustrated construction, outlet 18 of syringe 11 extends through a Luer tip 21 that is formed integrally with sleeve 16 and that serves as a mount for a hypodermic needle. However, the outlet tip 21 for syringe 11 may have a configuration for fitting into the inlet of a nebulizer, if syringe 11 is to be used as a nebulizer injector. Prior to use, as shown in FIGS. 1 and 2, the tip 21 of syringe 11 is preferably covered by a molded resin cap 22.

A finger engagement flange 23 is formed integrally with sleeve 17 at the inlet end of the housing for syringe 11. Also molded integrally with sleeve 17 is a rearwardly extending flange 24 upon which the connecting sleeve 13 is mounted.

A valve-seal member 25 is mounted within barrel 15 of syringe 11 near its outlet 18. Valve-seal member 25 is of molded rubber or other suitable elastomer material and is of hollow construction, having a central cavity 26. The forward wall of member 25 includes a displaceable plug 27 that normally affords a liquid-tight seal sealing the outlet end of the housing of syringe 11. An opening 28 in the rear wall of member 25 provides communication with the interior of barrel 15. A post 29 formed integrally with tip 16 projects rearwardly of the front wall 31 of the housing in alignment with plug 27.

Another valve-seal member 32 is mounted in barrel 15 at the inlet end of the housing for syringe 11, within the portion of barrel 15 encompassed by sleeve 17. Member 32 is also of molded rubber or other suitable elastomer material and has a threaded recess 33 facing toward the inlet opening 19 of the syringe. The inner wall 34 of member 32 comprises a slit valve 35 that is actuatable from a normal closed condition, shown in FIGS. 2 and 5A, to an open condition, shown in FIGS. 3 and 5B, by engagement with a fill needle 36. As shown in FIG. 2, the two valve-seal members 25 and 32, in conjunction with the housing of syringe 11, particularly barrel 15, define a normally sealed mixing chamber 38 containing a first medication ingredient 39 shown as a powder. Ingredient 39 could also be of liquid form.

Carrier syringe 12, as illustrated, is basically similar in construction to mixer-dispenser syringe 11. Thus, syringe 12 comprises a housing including a glass barrel 45, a molded resin sleeve 46 on the outlet end of the barrel, and a molded resin sleeve 47 on the inlet end of the barrel.

The outlet opening 48 of syringe 12 extends through the front wall 61 of sleeve 46. At one side of wall 61, there is a Luer tip 51 molded integrally with sleeve 46, upon which fill needle 36 is mounted. An integral construction for tip 51 and needle 36 could be used. On the inner side of wall 61 there is an integral molded post 59. A support sleeve 52 that is an extension of member 46 affords a mounting surface for the connecting sleeve 13. Within the forward or outlet end of barrel 45, there is positioned a discharge valve-seal member 55 corresponding in construction to the valve-seal member 25 of syringe 11; member 55 normally seals the outlet end of the housing or syringe 12. The front wall of valve-seal member 55 includes a knockout plug 57 that is aligned with post 59.

At the rear or inlet end of syringe 12, a finger-engagement flange 53 is formed integrally with sleeve 47. A piston-seal member 62 having a threaded outwardly facing recess 63 and incorporating a slit valve 65 is mounted within the inlet end portion of barrel 45, normally sealing the inlet end 49 of the housing of syringe 12. Thus, members 55 and 62, taken in conjunction with the barrel 45 that constitutes the principal housing member for syringe 12, define a storage chamber 68 containing a second medication ingredient 69, usually a liquid.

For shipping or storage purposes, plunger 14 is usually separated from the remainder of dispenser 10. A cap 71 may be mounted on the outer portion of sleeve 47 of syringe 12, as shown in FIG. 1. The two syringes 11 and 12 may also be separated for shipment, preferably with sleeve 13 mounted on syringe 12. When shipped with the syringes separated, a sterile shipping pouch should be employed.

Syringes 11 and 12, as illustrated, are commercial syringes of the kind manufactured and sold in substantial quantities by MPL, Inc., under the trademark SOLOPAK, for use as hypodermic syringes or nebulizer injectors. The basic construction of the individual syringes is shown in U.S. Pat. Nos. 3,803,700, 3,729,031, 3,729,032 3,885,297, and 3,889,351. The component parts may be identical with those employed in the commercial single-ingredient syringes, except that it may be desirable to extend the support sleeves 24 and 52 to a length sufficient to afford adequate support for the ends of the connecting sleeve 13. Sleeve 13 is a simple molded sleeve of elastomer or flexible thermoplastic resin material that fits tightly enough onto sleeves 24 and 52 to afford a sealed chamber 72 protecting the sterility of fill needle 36, yet not so tightly as to preclude release of sleeve 13 from sleeve 24, as described below.

Assembly of the complete dual-ingredient medication dispenser 10, in the form shown in FIGS. 1 and 2, can readily be effected without contaminating the ingredients 39 and 69 by premature mixing and without loss of sterility. Filling syringes 11 and 12 is simple and expedient because their construction is standard and filling equipment that can be maintained in sterile condition is readily available. The assembly of the complete dispenser 10 is facilitated when both of the syringes 11 and 12 are of the kind permitting filling from the rear or inlet end of the syringe, as shown; however, a front-fill syringe could be used for the carrier syringe 12 if desired. The mixer-dispenser syringe 11, on the other hand, must be rear fill device for effective operation of the invention.

In using dispenser 10, the first step is to push syringe 12 toward syringe 11, moving fill needle 36 through recess 33 in the inlet valve-seal member 32 until the fill needle opens the slit valve 35 as shown in FIGS. 3 and 5B. In the course of this movement, sleeve 13 is collapsed or distorted outwardly, as shown in FIG. 3, exposing a vent hole 75 in the connecting sleeve. Thus, when the position shown in FIG. 3 is reached, there is an effective vent for the previously sealed chamber 72 encompassing fill needle 36 and for syringe 11, as required for filling that syringe.

After fill needle 36 has been inserted through slit valve 35, plunger 14, threaded into recess 63 in piston-seal member 62, is driven inwardly of the barrel 45 of syringe 12 in the direction of arrow A (FIG. 3) forcing member 62 through barrel 45. The resulting pressure on valve-seal member 55 drives that member in the same direction, bringing plug 57 into engagement with the end of post 59. Further movement of valve-seal member 55 causes post 59 to dislodge plug 57, depositing the plug in the internal cavity of member 55. This effectively opens the outlet 48 of syringe 12 into communication with fill needle 36.

Subsequent continuing movement of piston movement 62 in the direction of arrow A discharges the liquid medication 69 from chamber 68 of syringe 12 through fill needle 36 into chamber 38 of syringe 11 and hence into contact with ingredient 39. When all or virtually all of the liquid ingredient 69 has been discharged into syringe 11, upon engagement of the two seal members 62 and 55 at the outlet end of syringe 12, the user grasps sleeve 13 and pulls this connecting sleeve off of the support sleeve 24 of syringe 11. This also removes fill needle 36 from its prior engagement in slit valve 35 of member 32 and separates syringe 12 completely from syringe 11.

It is now possible to shake or otherwise agitate syringe 11, thoroughly mixing the two medication ingredients 39 and 69. When this has been accomplished, plunger rod 14 is threaded into recess 33 in valve-seal member 32 as shown in FIG. 4 and syringe 11 is ready for use, administering the dual-ingredient medication in conventional manner. Of course, for administration of the medication, cap 22 must be removed from the outlet end of syringe 11. The operation of syringe 11 in administration of the medication corresponds fully to the operation of syringe 12 in filling syringe 11, as described above.

From the foregoing description, it will be seen that the dual-ingredient medication dispenser 10 is constructed almost entirely of conventional components and requires little or no special structural elements. Thus, the two syringes 11 and 12 preferably constitute conventional commercial rear-fill syringes, which are quite inexpensive because they are already in mass manufacture. Fill needle 36 is also a conventional and standard commercial part. Sleeve 13 is simple and inexpensive to manufacture and adds little to the cost of the dispenser. Plunger rod 14 is also an inexpensive conventional article.

The manipulative steps required for use of dispenser 10 are quite simple and obvious to the user. For utilization of the dispenser, the two syringes are moved together to the position of FIG. 3, collapsing sleeve 13. Plunger rod 14 is screwed into seal member 62 and employed to discharge the contents of syringe 12 into syringe 11. The two syringes are then separated, syringe 11 is shaken to mix the ingredients 39 and 69, and the dual-ingredient medication is then dispensed through the outlet 18,21 of syringe 11, using plunger rod 14 for syringe 11 as shown in FIG. 4.

In storage or transportation, dispenser 10 maintains the two ingredients 39 and 69 thoroughly separated. The two liquid and vapor seals afforded by the seal members 55 and 32 give double assurance that there will be no premature mixing of the ingredients 39 and 69. By the same token, because the entire dispenser assembly is fully sealed, loss of sterility for either syringe (or their contents) is precluded. Fill needle 36 is already fitted to syringe 12 and does not come into contact with the air until after insertion into valve-seal member 32 has been commened, so that loss of sterility in this regard is also minimized. Indeed, any contact of air with the interior or contents of the syringes is prevented at all times.

FIGS. 6 through 10 illustrate a dual-ingredient medication dispenser 100 constructed in accordance with another and preferred embodiment of the present invention. Dispenser 100 comprises a mixer-dispenser syringe 11, a carrier syringe 12, and a plunger rod 14 that is used with both syringes. The two syringes and the plunger rod may correspond fully to the construction described above in conjunction with FIGS. 1-4.

The dual-ingredient dispenser 100, however, incorporates a connecting means 113, for releasably interconnecting syringes 11 and 12, that is substantially different from sleeve 13 in dispenser 10. Thus, the syringe connection 113 comprises a relatively rigid sleeve 114, preferably of molded thermoplastic material, mounted on the extension 51 of the outlet-end sleeve 46 of carrier syringe 12. An interference fit may be employed between extension 51 and sleeve 114. Alternatively, sleeves 46 and 114 may be molded integrally as a single piece. In fact, sleeves 46 and 114 and fill needle 36 can all be molded as a single unit, though this has the disadvantage that the use of standard components usable in conventional single-ingredient syringes is no longer retained.

The syringe connection means 113 further comprises a second sleeve 115 mounted on sleeve 114. Sleeve 115 is tack-welded at 124 to a series of longitudinal ribs 116 on sleeve 114. Ribs 116 are used to afford vent passages through connecting means 113; they could be formed on the interior of sleeve 115 if desired. A single vent passage would be sufficient, if preferred. Ridges 118 on ribs 116 limit telescoping movement of sleeves 114 and 115, as described hereinafter. An interior flange 117 on sleeve 115 engages the flange 24 on the inlet end sleeve 17 of syringe 11 when the dispenser 100 is assembled as shown in FIG. 7.

Dispenser 100 may be shipped in three separate pieces, as shown in FIG. 6, preferably packaged in a sealed sterile pouch. Alternatively, the two syringes 11 and 12 may be connected by connecting means 113 prior to shipment, as in FIG. 7. Again, shipment in a sealed sterile pouch is preferred.

In using dispenser 100, the dispenser is assembled as shown in FIG. 7. Syringe 12 is then pushed toward syringe 11, telescoping sleeve 114 moving fill needle 36 into the inlet valve-seal member 32 to open slit valve 35 (FIG. 9). To effect this telescoping movement, the tack welds between sleeves 114 and 115 are broken; readily frangible welds are employed. When the position shown in FIG. 9 is reached, there is an effective vent for syringe 11, as required for filling that syringe, through the spaces between ribs 116 around the periphery of sleeve 114 and out to the atmosphere as indicated by arrows B.

Plunger 14 is then driven inwardly of the barrel 45 of syringe 12 (arrow A, FIG. 9), forcing member 62 through barrel 45 to discharge the liquid medication ingredient 69 from chamber 68 of syringe 12 through fill needle 36 into chamber 38 of syringe 11 and hence into contact with ingredient 39. When essentially all of the liquid ingredient 69 has been discharged into syringe 11, the user pulls connecting sleeve 115 off of the support sleeve 24 of syringe 11, separating syringe 12 completely from syringe 11. Shaking syringe 11 mixes the two medication ingredients 39 and 69 and syringe 11 is ready for use (see FIG. 10) to administer the dual-ingredient medication in conventional manner. Of course, for administration of the medication, cap 22 must be removed from the outlet end of syringe 11. A hypodermic needle 118 may be installed on syringe 11.

As in the case of dispenser 10, the dual-ingredient medication dispenser 100 is constructed almost entirely of conventional components. The two syringes 11 and 12 preferably constitute conventional commercial single-use rear-fill syringes; fill needle 36 is a standard commercial part; sleeves 114 and 115 are simple and inexpensive to manufacture and add little to the cost of the dispenser. The simple manipulative steps for use of dispenser 100 are the same as for dispenser 10.

In storage or transportation, dispenser 10 maintains the two ingredients 39 and 69 thoroughly separated, even when the dispenser is fully assembled. There is no premature mixing of the ingredients 39 and 69, and loss of sterility for either syringe (or their contents) is effectively minimized. Fill needle 36 is already fitted to syringe 12 in protected position within sleeves 114, 115, and requires no manipulation, further minimizing possible loss of sterility.

FIGS. 11 and 12 illustrate another connecting means 213 that may be utilized in assembling a mixer-dispenser syringe according to the invention. In connection with this embodiment, the syringes themselves have not been shown because the syringe construction is conventional and merely duplicates that of the earlier embodiments.

Connecting means 213 comprises a first sleeve member 214 that fits onto the outlet end of the carrier syringe. Sleeve 214 extends into a second connecting sleeve 215 having a flange 217 for mounting on the inlet end of the mixer-dispenser syringe. Sleeve 214 has a key 216 that fits into a slot 222 in sleeve 215, keying the two sleeves together to preclude relative rotation therebetween. A small vent aperture 219 is formed in the outer end of connecting sleeve 214 in a position in which it is effectively closed by the encompassing sleeve 215. Sleeve 215, in turn, is provided with a vent aperture 218. Vent aperture 218 is covered by a cap 221 for shipment.

In use, the dual ingredient medication dispenser employing the connecting means 213 of FIGS. 11 and 12 functions in essentially the same manner as described above for dispenser 100 of FIGS. 6-10. Before the two syringes are connected together, cap 221 is removed. This can be done immediately prior to use of the medication dispenser, so that the outer portion of the outlet end of carrier syringe 12, encompassing fill needle 36, is completely enclosed at all times prior to actual use. When the two syringes are moved together, breaking the tack weld 224 between sleeves 214 and 215, the two vent apertures 218 and 219 are moved into alignment with each other so that adequate venting is effected during discharge of the liquid medication ingredient from the carrier syringe into the mixer-dispenser syringe. It is thus seen that the embodiment of FIGS. 11 and 12 affords the same basic advantages as the previously described embodiments.

In the foregoing description, the invention is described as employed in conjunction with combination glass-plastic syringes. It will be recognized, of course, that it is equally applicable to syringes of all plastic construction.

We claim:

1. A dual ingredient medication dispenser comprising:

a mixer-dispenser syringe including a housing having an outlet end and an inlet end, a dispensing valve-seal member normally sealing the outlet end of the housing, an inlet valve-seal member normally sealing the inlet end of the housing, the inlet valve-seal member being actuatable from a normal closed condition to an open condition by engagement with a fill needle, with the mixer-dispenser syringe housing and its two valve-seal members defining a mixing chamber containing a first medication ingredient;

a carrier syringe including a housing having an outlet end and an inlet end, a fill needle projecting outwardly from the outlet end of the housing, a discharge valve-seal member normally sealing the outlet end of the housing, and a piston-seal member normally sealing the inlet end of the housing, with the carrier syringe housing, the piston member, and the discharge valve-seal member defining a storage chamber containing a second medication ingredient;

and connecting means, comprising a connecting sleeve, for releasably connecting the outlet end of the carrier syringe to the inlet end of the mixer dispenser syringe with the fill needle aligned with the inlet valve-seal member of the mixer-dispenser syringe, but permitting movement of the two syringes together to engage the fill needle with the inlet valve-seal member of the mixer-dispenser syringe for discharge of the second medication ingredient into the mixing chamber without requiring removal of the sleeve; the connecting sleeve being a length of tubing of flexible material which includes a normally closed vent aperture which is opened whenever the two syringes are moved together sufficiently to engage the fill needle with the inlet valve-seal member of the mixer-dispenser syringe.

2. A dual-ingredient medication dispenser, according to claim 1, in which the connecting sleeve is mounted on each syringe by a tight, expansion fit on one end of the syringe housing.

3. A dual-ingredient medication dispenser, according to claim 1, in which the connecting sleeve is a length of tubing formed of rubber or like elastomer material.

4. A dual-ingredient medication dispenser, according to claim 1 in which the connecting sleeve is a length of flexible resin tubing.

5. A dual ingredient medication dispenser comprising:

a mixer-dispenser syringe including a housing having an outlet end and an inlet end, a dispensing valve-seal member normally sealing the outlet end of the housing, an inlet valve-seal member normally sealing the inlet end of the housing, the inlet valve-seal member being actuatable from a normal closed condition to an open condition by engagement with a fill needle, with the mixer-dispenser syringe housing and its two valve-seal members defining a mixing chamber containing a first medication ingredient;

a carrier syringe including a housing having an outlet end and an inlet end, a fill needle projecting outwardly from the outlet end of the housing, a discharge valve-seal member normally sealing the outlet end of the housing, and a piston-seal member normally sealing the inlet end of the housing, with the carrier syringe housing, the piston member, and the discharge valve-seal member defining a storage chamber containing a second medication ingredient;

and connecting means for releasably connecting the outlet end of the carrier syringe to the inlet end of the mixer dispenser syringe with the fill needle aligned with the inlet valve-seal member of the mixer-dispenser syringe, but permitting movement of the two syringes together to engage the fill needle with the inlet valve-seal member of the mixer-dispenser syringe for discharge of the second medication ingredient into the mixing chamber without requiring removal of the sleeve;

the connecting means comprising two relatively rigid connecting sleeves fitted together in telescoping relation, one of the connecting sleeves being mountable on the outlet end of the carrier syringe in encompassing relation to the projecting portion of the fill needle, and the other connecting sleeve being engageable with the inlet end of the mixer-dispenser syringe housing;

the surface of one of the connecting sleeves that engages the other sleeve being formed with at least one longitudinal vent passage which vents the mixer-dispenser syringe during discharge of the second medication ingredient into the mixing chamber.

6. A dual ingredient medication dispenser comprising:

a mixer-dispenser syringe including a housing having an outlet end and an inlet end, a dispensing valve-seal member normally sealing the outlet end of the housing, an inlet valve-seal member normally sealing the inlet end of the housing, the inlet valve-seal member being actuatable from a normal closed condition to an open condition by engagement with a fill needle, with the mixer-dispenser syringe housing and its two valve-seal members defining a mixing chamber containing a first medication ingredient;

a carrier syringe including a housing having an outlet end and an inlet end, a fill needle projecting outwardly from the outlet end of the housing, a discharge valve-seal member normally sealing the outlet end of the housing, and a piston-seal member normally sealing the inlet end of the housing, with the carrier syringe housing, the piston member, and the discharge valve-seal member defining a storage chamber containing a second medication ingredient;

and connecting means for releasably connecting the outlet end of the carrier syringe to the inlet end of the mixer dispenser syringe with the fill needle aligned with the inlet valve-seal member of the mixer-dispenser syringe, but permitting movement of the two syringes together to engage the fill needle with the inlet valve-seal member of the mixer-dispenser syringe for discharge of the second medication ingredient into the mixing chamber without requiring removal of the sleeve;

the connecting means comprising two connecting sleeves fitted together in telescoping relation, one of the two connecting sleeves being mountable on the outlet end of the carrier syringe in encompassing relation to the projecting portion of the fill needle, and the other connecting sleeve being engageable with the inlet end of the mixer-dispenser syringe housing;

the two connecting sleeves being joined by a frangible connection that is broken when the two syringes are moved together.

7. A dual ingredient medication dispenser comprising:

a mixer-dispenser syringe including a housing having an outlet end and an inlet end, a dispensing valve-seal member normally sealing the outlet end of the housing, an inlet valve-seal member normally sealing the inlet end of the housing, the inlet valve-seal member being actuatable from a normal closed condition to an open condition by engagement with a fill needle, with the mixer-dispenser syringe housing and its two valve-seal members defining a mixing chamber containing a first medication ingredient;

a carrier syringe including a housing having an outlet end and an inlet end, a fill needle projecting outwardly from the outlet end of the housing, a discharge valve-seal member normally sealing the outlet end of the housing, and a piston-seal member normally sealing the inlet end of the housing, with the carrier syringe housing, the piston member, and the discharge valve-seal member defining a storage chamber containing a second medication ingredient;

and connecting means for releasably connecting the outlet end of the carrier syringe to the inlet end of the mixer dispenser syringe with the fill needle aligned with the inlet·valve-seal member of the mixer-dispenser syringe, but permitting movement of the two syringes together to engage the fill needle with the inlet valve-seal member of the mixer-dispenser syringe for discharge of the second medication ingredient into the mixing chamber without requiring removal of the sleeve;

the connecting means comprising two relatively rigid connecting sleeves fitted together in telescoping relation, one of the two connecting sleeves being mountable on the outlet end of the carrier syringe in encompassing relation to the projecting portion of the fill needle, and the other connecting sleeve being engageable with the inlet end of the mixer-dispenser syringe housing;

the innermost connecting sleeve including a first vent aperture which is normally covered by the outermost sleeve, and the outermost sleeve including a second vent aperture which is brought into alignment with the first vent aperture when the two sleeves are telescoped by movement of the two syringes toward each other;

the connecting means further including a removable mask for said second vent aperture.

8. A dual-ingredient medication dispenser, according to claim 7, in which the two connecting sleeves are keyed together to preclude relative rotation thereof.

9. A dual-ingredient medication dispenser, according to claim 8, in which the two connecting sleeves are joined by a frangible connection that is broken when the two syringes are moved together.

* * * * *